US00PP17014P2

(12) United States Plant Patent
Vink

(10) Patent No.: US PP17,014 P2
(45) Date of Patent: Aug. 22, 2006

(54) ***CAMELLIA* PLANT NAMED 'CURLY LADY'**

(50) Latin Name: *Camellia japonica*
Varietal Denomination: Curly Lady

(75) Inventor: Hubertus Jozef Maria Vink, Beugen (NL)

(73) Assignee: Witteman & Co., Hillegom (NL)

( * ) Notice: Subject to any disclaimer, the term of this patent is extended or adjusted under 35 U.S.C. 154(b) by 97 days.

(21) Appl. No.: 11/046,018

(22) Filed: Jan. 28, 2005

(51) Int. Cl.
*A01H 5/00* (2006.01)

(52) U.S. Cl. ..... Plt./245

(58) Field of Classification Search ..... Plt./245, Plt./244

See application file for complete search history.

*Primary Examiner*—Kent Bell
*Assistant Examiner*—Louanne Krawczewicz Myers
(74) *Attorney, Agent, or Firm*—C. A. Whealy

(57) ABSTRACT

A new and distinct cultivar of *Camellia* plant named 'Curly Lady', characterized by its upright and outwardly spreading plant habit; spirally twisting lateral branches; freely branching growth habit; glossy dark green-colored leaves; and large semi-double red-colored flowers.

2 Drawing Sheets

Botanical designation: *Camellia japonica.*
Cultivar denomination: 'Curly Lady'.

BACKGROUND OF THE INVENTION

The present Invention relates to a new and distinct cultivar of *Camellia*, botanically known as *Camellia japonica*, and hereinafter referred to by the name 'Curly Lady'.

The new *Camellia* is a naturally-occurring branch mutation of the *Camellia japonica* cultivar Lady Campbell, not patented. The new *Camellia* was discovered and selected as a branch mutation on a single plant of 'Lady Campbell' by the Inventor in 1999 in a controlled environment in Beugen, The Netherlands.

Asexual reproduction of the new *Camellia* by terminal cuttings taken in a controlled environment in Beugen, The Netherlands since 1999, has shown that the unique features of this new *Camellia* are stable and reproduced true to type in successive generations.

SUMMARY OF THE INVENTION

The new *Camellia* has not been observed under all possible environmental conditions. The phenotype may vary somewhat with variations in environment such as temperature, daylength and/or light intensity without, however, any variance in genotype.

The following traits have been repeatedly observed and are determined to be the unique characteristics of 'Curly Lady'. These characteristics in combination distinguish 'Curly Lady' as a new and distinct cultivar:

1. Upright and outwardly spreading plant habit.
2. Spirally twisting lateral branches.
3. Freely branching growth habit.
4. Glossy dark green-colored leaves.
5. Large semi-double red-colored flowers.

Plants of the new *Camellia* differ primarily from plants of the parent, the cultivar Lady Campbell, in lateral branch orientation as plants of the cultivar Lady Campbell have straight, not twisting, lateral branches.

Plants of the new *Camellia* can also be compared to plants of the *Camellia* cultivar TDN 1116, disclosed in U.S. Plant Pat. No. 14,213. Plants of the new *Camellia* differed from plants of the cultivar TDN 1116 primarily in lateral branch orientation as plants of the cultivar TDN 1116 have straight, not twisting, lateral branches.

BRIEF DESCRIPTION OF THE PHOTOGRAPHS

The accompanying colored photographs illustrate the overall appearance of the new *Camellia*. These photographs show the colors as true as it is reasonably possible to obtain in colored reproductions of this type. Colors in the photographs may differ slightly from the color values cited in the detailed botanical description, which accurately describe the colors of the new *Camellia.*

The photograph on the first sheet comprises a side perspective view of a typical flowering plant of 'Curly Lady' grown in a container.

The photograph at the top of the second sheet is a close-up view of a typical flower of 'Curly Lady'.

The photograph in the middle of the second sheet is a close-up view of a typical lateral branch of 'Curly Lady'.

The photograph at the bottom of the second sheet is a close-up view of a typical leaf of 'Curly Lady'.

DETAILED BOTANICAL DESCRIPTION

The new *Camellia* has not been observed under all possible environmental conditions. The phenotype may vary somewhat with variations in environment such as temperature and light intensity, without, however, any variance in genotype.

The aforementioned photographs, following observations and measurements describe plants grown in 7.5-liter containers in Boskoop, The Netherlands, in an outdoor nursery and under commercial production practices. Plants used for the photographs and the description were about four years old. The photographs and description were taken during the spring with day temperatures ranging from 3 to 20° C. and night temperatures ranging from 0 to 10° C. In the following description, color references are made to The Royal Horticultural Society Colour Chart, 2001 Edition, except where general terms of ordinary dictionary significance are used.

Botanical classification: *Camellia japonica* 'Curly Lady'.

Parentage: Naturally-occurring branch mutation of the *Camellia japonica* cultivar Lady Campbell, not patented.

Propagation:

*Type*.—By terminal vegetative cuttings.

*Time to produce a rooted young plant*.—About two months at temperatures of about 16° C.

*Root description*.—Moderate thickness, fleshy; white in color.

*Rooting habit*.—Freely branching.

Plant description:

*Plant form and growth habit*.—Perennial, evergreen; upright and outwardly spreading plant habit; broad inverted triangle; moderately vigorous.

*Branching habit*.—Freely branching, about six lateral branches.

*Plant height, soil level to top of flowers*.—About 50 cm.

*Plant diameter, area of spread*.—About 47 cm.

*Lateral branch description*.—Length: About 29 cm. Diameter at base: About 4 mm. Internode length: About 3.5 cm. Strength: Moderately strong to strong. Texture: Smooth, glabrous. Orientation: Spirally twisting. Color: Young: 146A. Mature: 200D to between 199B to 199C.

*Foliage description*.—Arrangement: Alternate, simple. Length: About 9.5 cm. Width: About 4 cm. Shape: Ovate. Apex: Apiculate. Base: Obtuse. Margin: Serrate. Orientation: Undulate; occasionally curled. Venation pattern: Pinnate. Texture, upper and lower surfaces: Leathery; smooth, glabrous. Luster, upper surface: Glossy. Luster, lower surface: Somewhat glossy. Color: Developing foliage, upper surface: Much darker green than 146A. Developing foliage, lower surface: 146A. Fully expanded foliage, upper surface: Slightly darker than 139A; venation, 143A to 143B. Fully expanded foliage, lower surface: Between 143A and 146A; venation, 144A to 144B. Petiole: Length: About 1 cm. Diameter: About 3 mm. Texture, upper and lower surfaces: Smooth, glabrous. Color, upper and lower surfaces: 144A to 144B to 147A.

Flower description:

*Flower arrangement*.—Flowers arranged singly at terminals with usually about eight flowers per plant. Flowers face upward or outward.

*Flower appearance*.—Semi-double flower form with numerous petals and petaloids.

*Natural flowering season*.—Late March in The Netherlands. Flowers not persistent.

*Flower longevity*.—Flowers maintain good substance for about one week.

*Fragrance*.—None detected.

*Flower diameter*.—About 8.3 cm.

*Flower depth*.—About 3.8 cm.

*Flower bud* (*about five days before opening*).—Length: About 2.8 cm. Diameter: About 2.2 mm. Shape: Broadly ovoid. Color: Towards the base, 145A to 145B; towards the apex, 53B.

*Petals/petaloids*.—Arrangement: Semi-double flower form; numerous whorls of about 72 imbricate petals and petaloids. Length, largest petals: About 4.1 cm. Width, largest petals: About 3.8 cm. Shape: Broadly obovate to orbicular. Apex: Rounded. Margin: Entire. Texture, upper and lower surfaces: Smooth, glabrous; velvety. Color: When opening, upper surface: 47B; towards the margins, 47C. When opening, lower surface: 46C; towards the margins, 46D. Fully opened, upper surface: 46C; towards the margins, 46D; color becoming closer to 47C to 47D with development. Fully opened, lower surface: 46C.

*Sepals*.—Arrangement: Single whorl of about four sepals. Length: About 2.3 cm. Width: About 1.8 cm. Shape: Broadly oval. Apex: Rounded. Base: Cuneate. Margin: Entire. Texture, upper and lower surfaces: Smooth, glabrous. Color: When opening, upper surface: 145C to 145D; towards the base, 50C. When opening, lower surface: 145B to 145C; towards the base, 50C. Fully opened, upper and lower surfaces: 145B to 145C; towards the base, 51C to 51D.

*Peduncles*.—Length: About 3 mm. Diameter: About 4 mm. Angle: Mostly horizontal. Strength: Strong. Texture: Smooth, glabrous. Color: 150B.

*Reproductive organs*.—Androecium: Quantity of stamens per flower: Two to 26. Filament length: About 1.5 cm. Anther length: About 3 mm. Anther shape: Oval. Anther color: 22C. Amount of pollen: Moderate. Pollen color: 14A. Gynoecium: Quantity of pistils per flower: Three. Pistil length: About 1.9 cm. Style length: About 1.8 cm. Style color: 62D. Stigma shape: Obtuse. Stigma diameter: Less than 1 mm. Stigma color: 150D. Ovary color: 37C to 37D.

*Seed/fruit*.—Seed and fruit development have not been observed.

Weather/temperature tolerance: Plants of the new *Camellia* have been observed to be very tolerant to rain and wind. Plants of the new *Camellia* have been observed to tolerate temperatures from −10 to 35° C.

Disease/pest resistance: Plants of the new *Camellia* have not been observed to be resistant to pathogens and pests common to *Camellias*.

It is claimed:

1. A new and distinct *Camellia* plant named 'Curly Lady', as illustrated and described.

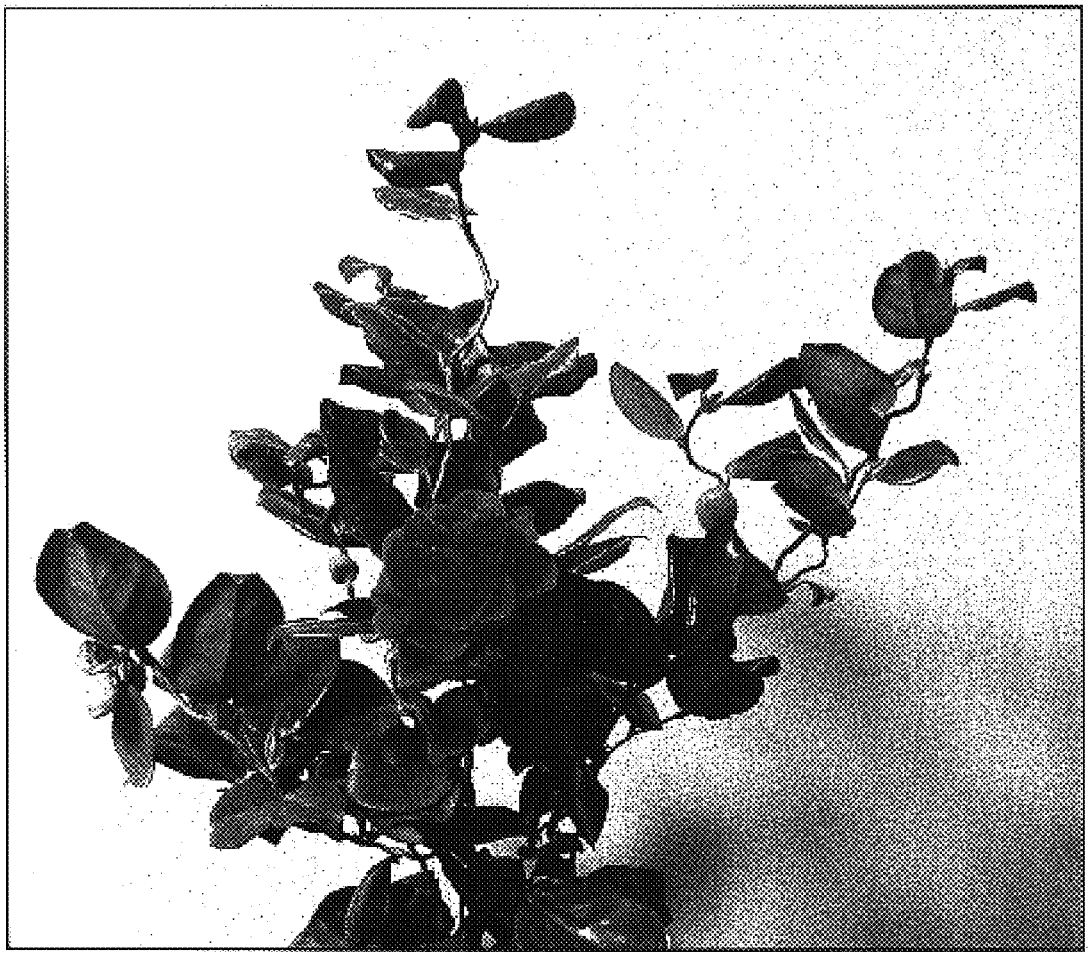

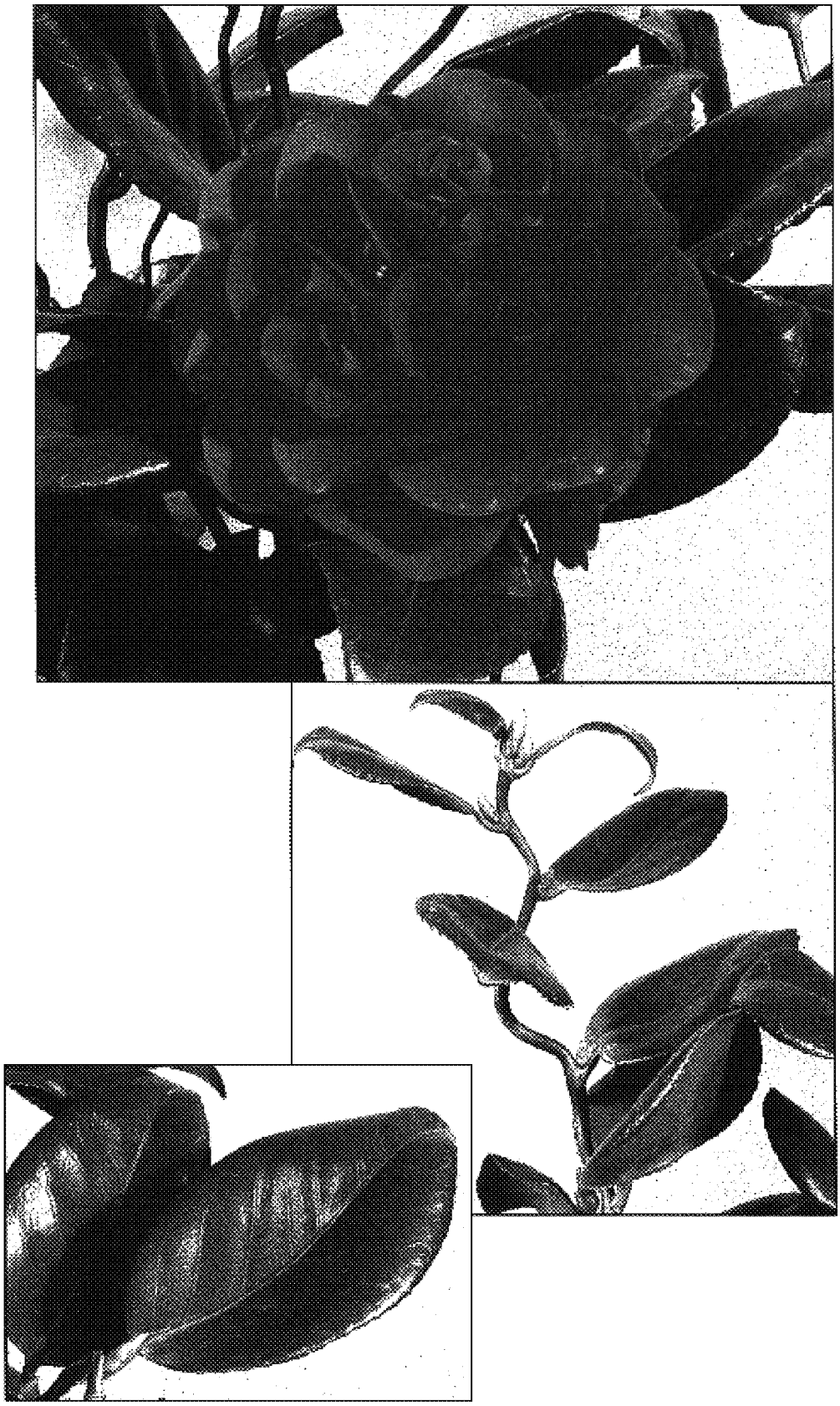

* * * * *